United States Patent [19]

Marler et al.

[11] Patent Number: 4,967,020

[45] Date of Patent: Oct. 30, 1990

[54] PROCESS FOR THE HYDRATION OLEFINS

[75] Inventors: David O. Marler, Deptford, N.J.; Charles M. Sorensen, Wilmington, Del.; Philip Varghese, Singapore, Singapore

[73] Assignee: Mobil Oil Corporation, Fairfax, Va.

[21] Appl. No.: 389,198

[22] Filed: Aug. 3, 1989

Related U.S. Application Data

[63] Continuation-in-part of Ser. No. 139,565, Dec. 30, 1987, abandoned.

[51] Int. Cl.$^5$ ................... C07C 29/04; C07C 31/10
[52] U.S. Cl. .................................... 568/896; 568/897
[58] Field of Search ...................... 568/895, 896, 897

[56] References Cited

U.S. PATENT DOCUMENTS 4,214,107  7/1980  Chang et al. .................. 568/897
4,783,555  11/1988  Atkins .......................... 568/897

Primary Examiner—J. E. Evans
Attorney, Agent, or Firm—Alexander J. McKillop; Charles J. Speciale; Malcolm D. Keen

[57] ABSTRACT

A process for converting propylene to isopropyl alcohol by contacting water with a propylene-containing feed at a mole ratio of water to propylene of at least about 0.5:1 (water:olefin), usually about 1:1–10:1 in the vapor and/or liquid phase under propylene hydration conditions. The hydration is carried out in the presence of a relatively constrained intermediate pore size zeolite such as ZSM-35 or ferrierite as the hydration catalyst. The zeolite is used in the acid form and with a crystal size of not more than $0.2\mu$ to give high activity for conversion to isopropyl alcohol.

15 Claims, No Drawings

PROCESS FOR THE HYDRATION OLEFINS

CROSS-REFERENCE TO RELATED APPLICATIONS

This application is a continuation-in-part of prior co-pending Application Ser. No. 07/139,565, filed Dec. 30, 1987 and now abandoned. The contents of application Ser. No. 07/139,565 are incorporated in this application by reference.

FIELD OF THE INVENTION

This invention relates to a process for the catalytic hydration of propylene to provide isopropyl alcohol in enhanced amounts. The process employs the acidic form of certain natural or synthetic porous crystalline materials or zeolites, especially the constrained intermediate pore size zeolites such as ferrierite and the synthetic zeoites such as ZSM-22, ZSM-23 and ZSM-35 as the catalyst. The product isopropyl alcohol is useful as a solvent, a chemical intermediate and as a high octane blending component for gasoline.

BACKGROUND OF THE INVENTION

There is a need for an efficient catalytic process to manufacture alcohols from light olefins to augment the supply of high octane blending stocks for gasoline. Lower molecular weight alcohols such as isopropyl alcohol (IPA) are in the gasoline boiling range and are known to have a high blending octane number. In addition, by-product propylene from which IPA can be made is usually available at low cost in a petroleum refinery.

The catalytic hydration of olefins to provide alcohols is a well-established art and is of significant commercial importance. Representative olefin hydration processes are disclosed in U.S. Pat. Nos. 2,162,913; 2,477,380; 2,797,247; 3,798,097; 2,805,260; 2,830,090; 2,861,045; 2,891,999; 3,006,970; 3,198,752; 3,810,849; 3,989,762, among others.

Olefin hydration employing zeolite catalysts is known. As disclosed in U.S. Pat. No. 4,214,107, mono-olefins in the $C_{2-4}$ range, specifically, ethylene, propylene, n-butene-1 and cis and trans n-butene-2, are reacted with water at olefin:water mole ratios of from about 0.1:1 to 2:1, preferably from about 0.5:1 to 1.5:1 (equivalent to water:olefin mole ratios of from about 10:1 to about 0.5:1 and preferably from about 2:1 to about 0.67:1) to provide the corresponding alcohol, essentially free of ether and hydrocarbon by-product, employing as olefin hydration catalyst a zeolite having a Constraint Index of 1 to 12 as exemplified by ZSM-5, ZSM-11, ZSM-12, ZSM-35 and ZSM-38. Of the foregoing zeolites, only acidic ZSM-5 is illustrated in a working example.

According to U.S. Pat. No. 4,499,313, an olefin is hydrated to the corresponding alcohol in the presence of hydrogen-type mordenite or hydrogen-type zeolite Y each having a silica-alumina molar ratio of 20 to 500. The use of such a catalyst is said to result in higher yields of alcohol than olefin hydration processes which employ conventional solid acid catalysts. Use of the catalyst is said to offer the advantage over ion-exchange type olefin hydration catalysts of not being restricted by the hydration temperature. Reaction conditions employed in the process include a temperature of from 50°-300° C., preferably 100°-250° C., a pressure of 5 to 200 kg/cm² to maintain liquid phase or gas-liquid multiphase conditions and a mole ratio of water to olefin of from 1 to 20. The reaction time can be 20 minutes to 20 hours when operating batchwise and the liquid hourly space velocity (LHSV) is usually 0.1 to 10 in the case of continuous operation.

European Patent Application 210,793 describes an olefin hydration process employing a medium pore zeolite as hydration catalyst. Specific catalysts mentioned are Theta-1, said to be preferred, ferrierite, ZSM-22, ZSM-23 and NU-10.

SUMMARY OF THE INVENTION

We have now found that the activity of the more highly constrained intermediate pore size zeolites such as ferrierite and the synthetic ferrierite ZSM-35 for the production of alcohols may be enhanced by the use of the zeolite with a particular and specific crystal size. According to the present invention, the zeolite is used with a crystal size of not more than 0.2(microns). The improved activity of the small crystal size zeolite is especially notable at water:olefin ratios of 0.5:1 or higher, e.g. from 1:1 to about 10:1 (water:olefin).

According to the present invention, therefore, propylene is converted to isopropyl alcohol by contacting water with a propylene feed in a mole ratio of water to propylene of at least 0.5:1 in the vapor and/or liquid phase under propylene hydration conditions. The reaction is carried out in the presence of ferrierite or ZSM-35 which is at least partially in the acid or hydrogen form as the propylene hydration catalyst. The zeolite which is used has a crystal size of not more than $0.2\mu$. The product of the hydration is isopropyl alcohol and is obtained with relatively high selectivity and with high conversion levels of the propylene feed.

At water:propylene mole ratio of at least 0.5:1,e.g. 1:1 to 10:1, these zeolite hydration catalysts, especially ZSM-35 have been found to be far more effective as catalysts for the conversion of propylene to isopropyl alcohol than other acidic zeolites.

The isopropyl alcohol resulting from the propylene hydration process of this invention is advantageously employed as a blending component for gasoline, as a solvent and an as intermediate for a variety of industrial chemical syntheses.

DETAILED DESCRIPTION

The present invention is applicable to the hydration of essentially pure propylene or propylene in admixture with one or more materials which may or may not contain other hydratable olefins. Examples of propylene-containing streams which are particularly advantageous herein due to their low cost and ready availability where petroleum refineries are concerned include gas plant off-gas containing ethylene and propylene and refinery FCC propane/propylene streams. For example, a typical FCC light olefin stream possesses the composition shown in Table 1 below.

TABLE 1

| Typical Refinery FCC Light Olefin Composition | | |
|---|---|---|
| | Wt. % | Mole % |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.3 |

TABLE 1-continued

| Typical Refinery FCC Light Olefin Composition | | |
| --- | --- | --- |
| | Wt. % | Mole % |
| Pentanes | 0.7 | 0.4 |

In order to achieve high conversion of the propylene to the corresponding alcohol, the hydration is carried out at water:propylene mole ratios of at least 0.5:1 and preferably higher e.g. 2:1. Ratios of up to 10:1, usually not more than 5:1 are preferred.

The other operating conditions of the propylene hydration process are not especially critical and include a preferred temperature range of from about 200° to about 400° F., preferably from about 250° to about 350° F. and most preferably from about 280° to about 350° F. Total system pressure will normally be from at least about 5 atm, preferably at least about 20 atm and still more preferably at least about 40 atmospheres.

The hydration can be carried out under liquid phase, vapor phase or mixed vapor-liquid phase conditions in batch or continuous manner using a stirred tank reactor or fixed bed flow reactor, e.g., trickle-bed, liquid-up-flow, liquid-down-flow, counter-current, co-current, etc. Reaction times of from about 20 minutes to about 20 hours when operating in batch and an LHSV of from about 0.1 to about 10 when operating continuously are suitable. It is generally preferable to recover any unreacted propylene and recycle it to the reactor.

The catalyst employed in the propylene hydration process is a relatively constrained intermediate pore size zeolite, that is the zeolite has a Constraint Index in the range of 1-12, as determined by the method described in U.S. Pat. No. 4,016,218. The zeolites which are actually used in the present process, however, are also characterised by specific sorption properties related to their relatively constrained diffusion characteristics. These sorption characteristics are those which are set out in U.S. Pat. No. 4,810,357 for the zeolites such as zeolite ZSM-22, ZSM-23, ZSM-35 and ferrierite.

The zeolite hydration catalysts used in the present process are zeolites which have pore openings defined by: (1) a ratio of sorption of n-hexane to o-xylene, on a volume percent basis, of greater than about 3, which sorption is determined at a $P/P_o$ of 0.1 and at a temperature of 50° C. for n-hexane and 80° C. for o-xylene and (2) by the ability of selectively cracking 3-methylpentane (3MP) in preference to the doubly branched 2,3-dimethylbutane (DMB) at 1000° F. and 1 atmosphere pressure from a 1/1/1 weight ratio mixture of n-hexane/3-methyl-pentane/2,3-dimethylbutane, with the ratio of rate constants $k_{3MP}/k_{DMB}$ determined at a temperature of 1000° F. being in excess of about 2.

The expression, "$P/P_o$", is accorded its usual significance as described in the literature, for example, in "The Dynamical Character of Adsorption" by J.H. deBoer, 2nd Edition, Oxford University Press (1968) and is the relative pressure defined as the ratio of the partial pressure of sorbate to the vapor pressure of sorbate at the temperature of sorption. The ratio of the rate constants, $k_{3MP}/k_{DMB}$, is determined from 1st order kinetics, in the usual manner, by the following equation:

$$k = (1/T_c) \ln (1/1-\epsilon)$$

where k is the rate constant for each component, $T_c$ is the contact time and $\epsilon$ is the fractional conversion of each component.

Zeolites conforming to these sorption requirements include the naturally occurring zeolite ferrierite as well as the synthetic zeolites ZSM-22, ZSM-23 and ZSM-35. ZSM-35 is the preferred catalytic material for the present purposes. These zeolites are at least partly in the acid or hydrogen form when they are used in the present hydration process.

The preparation and properties of zeolite ZSM-22 are described in U.S. Pat. No.4,810,357 (Chester) to which reference is made for such a description.

The synthetic zeolite ZSM-23 is described in U.S. Pat. Nos. 4,076,842 and 4,104,151 to which reference is made for a description of this zeolite, its preparation and properties.

The intermediate pore-size synthetic crystalline material designated ZSM-35 ("zeolite ZSM-35" or simply "ZSM-35"), is described in U.S. Pat. No. 4,016,245, to which reference is made for a description of this zeolite and its preparation.

Ferrierite is a naturally-occurring mineral, described in the literature, see, e.g., D.W. Breck, ZEOLITE MOLECULAR SIEVES, John Wiley and Sons (1974), pages 125-127, 146, 219 and 625, to which reference is made for a description of this zeolite.

In general, the zeolitic propylene hydration catalyst employed in the present process will possess a silica to alumina ratio of at least about 10. In place of all or a part of the aluminum present in the framework structure of the zeolite, other trivalent acidic metals can be present such as gallium, iron, boron, etc.

The zeolite hydration catalyst used in the process will generally possess an alpha value of at least about 1, and preferably at least about 10. "Alpha value", or "alpha number", is a measure of zeolite acidic functionality and is more fully described together with details of its measurement in U.S. Pat. No. 4,016,218 J. Catalysis, 6, pp. 278-287 (1966) and J. Catalysis, 61, pp. 390-396 (1980). Low acidity values (alpha values of less than about 200) can be achieved by a variety of techniques including (a) synthesizing the zeolite with a high silica/alumina ratio, (b) steaming, (c) steaming followed by dealuminization and (d) substituting aluminum with one or more other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° F. with from about 10 to about 200 atmospheres. Specific details of several steaming procedures may be gained from the disclosures of U.S. Pat. Nos. 4,326,994, 4,374,296 and 4,418,235, the contents of which are incorporated by reference herein. Aside from or in addition to any of the foregoing procedures, the surface acidity of the zeolite can be eliminated or reduced by treatment with bulky reagents as described in U.S. Pat. No. 4,520,221, the contents of which are incorporated by reference herein.

The use of these zeolites, especially ZSM-35, as the propylene hydration catalyst results in high selectivity for isopropyl alcohol, especially at water:olefin ratios of 0.5:1 or higher and with zeolite crystal sizes of not more than 0.2μ. At temperatures from about 320° to 370° F. propylene conversion increases from about 33 to 41% at about 1500 psig system pressure but IPA selectivity remains high. This result contrasts with that obtained using zeolite Beta as hydration catalyst where high olefin oligomerisation selectivity limits the upper temperature of the process to about 360° to 380° F.

The effect of zeolite crystal size is shown in Table 2 below which shows the extent of propylene conversion at two different water:olefin ratios for three differently sized ZSM-35 and ferrierite crystals. The olefin hydration was carried out at 330° F., 1000 psig, 0.6 WHSV $C_3=$.

TABLE 2

| Zeolite, crystal Size, μ. | Percent $C_3 =$ conv. at $H_2O:C_3$ ratio | |
|---|---|---|
| | 2:1 | 0.5:1 |
| ZSM-35, <0.1 | 55 | 28 |
| ZSM-35, 0.1–0.2 | 45 | 27 |
| Ferrierite, 0.2–1.0 | 9 | 6 |

Thus, the smaller crystal size shows higher conversion, indicating that the reaction is crystal size dependant at water:olefin ratios above 0.5:1 and that pore diffusion limitations exist under these conditions.

In practicing the propylene hydration process of the present invention, it is usually advantageous to incorporate the zeolite with a matrix or binder material which is resistant to the temperature and other conditions employed in the process. Useful matrix materials include both synthetic and naturally-occurring substances, e.g., inorganic materials such as clay, silica and/or metal oxides. The latter can be either naturally-occurring or can be provided in the form of gelatinous precipitates or gels including mixtures of silica and metal oxides. Naturally-occurring clays may also be used as the binder or matrix material.

Among the synthetic oxides with which the zeolite can be composited with are porous matrix materials such as alumina, silica, titania, zirconia, silica-alumina, silica-magnesia, silica-zirconia, silica-thoria, silica-beryllia and silica-titania etc., as well as ternary oxide compositions such as silica-alumina-thoria, silica-alumina-zirconia, silica-alumina-magnesia and silica-magnesia-zirconia. The matrix can be in the form of a cogel. The relative proportions of zeolite and matrix material, on an anhydrous basis, can vary widely with the zeolite content ranging from between about 1 to about 99 wt%, and more usually in the range of about 5 to about 90 wt%, of the dry composite.

In some cases, it may be advantageous to formulate the zeolite hydration catalyst as an extrudate bound with a low acidity refractory oxide binder such as titania or silica since catalysts made with these low-acidity binders have been found to exhibit higher activity than similar catalysts bound with alumina or other more acidic type binders. Table 3 below shows the improved conversion of the propylene feed at 330° F., 1000 psig, 0.6 WHSV $C_3=$, 2:1 water:olefin.

TABLE 3

| Binder | TOS, hr | Percent $C_3$ Conv. |
|---|---|---|
| $Al_2O_3$ | 24 | 55 |
| $SiO_2$ | 54 | 70 |
| $TiO_2$ | 24 | 73 |

Under most conditions it has been found that selectivity for IPA is greater than 99%, regardless of binder type with small amounts of di-isopropyl ether and olefin oligomer, primarily hexene, being the only detectable by-products.

The catalysts made using the low acidity binders such as silica or titania can be made by the method described in commonly assigned U.S. patent applications Ser. No. 07/44,639, filed May 1, 1987 now abandoned and Serial No. 07/140,357, filed Jan. 4 1988, to which reference is made for a description of the method. In the method described in those applications, a homogeneous mixture of zeolite, water and a low acidity refractory oxide binder, e.g., silica, which contains at least an extrusion-facilitating amount of the binder in a colloidal state and which is substantially free of added alkali metal base and/or basic salt, is formed into an extrudable mass, the mass is extruded and the resulting extrudate is dried and calcined.

The original cations associated with the zeolite can be replaced by a wide variety of other cations employing techniques well known in the art, e.g., by ion-exchange. Typical replacing cations include hydrogen, ammonium, alkyl ammonium and metal cations, and their mixtures Metal cations can also be introduced into the zeolite. In the case of metal cations, particular preference is given to metals of Groups IB to VIII of the Periodic Table, including, by way of example, iron, nickel, cobalt, copper, zinc, palladium, calcium, chromium, tungsten, molybdenum, rare earth metals, etc. These metals can also be present in the form of their oxides.

A typical ion-exchange technique involves contacting the zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249, 3,140,251 and 3,140,253.

In the following Examples, the zeolites are in the acidic (i.e., the hydrogen) form and all percentages are by weight unless otherwise indicated.

Example 1

This example illustrates the preparation of an alumina-bound ZSM-35 catalyst composition employing pyrrolidine as the crystal structure forming agent.

Pyrrolidine in an amount of 3.2 weight parts was added to a mixture of 1.38 weight parts 50 weight percent aqueous sodium hydroxide, 1.18 weight parts of hydrated aluminum sulfate $(Al_2O_3(SO_4)_3.14H_2O)$, 3.2 weight parts amorphous precipitated silica (PPG Industries HiSil 233) and 7.5 weight parts deionized water. The reaction mixture was then heated to 220° F. and stirred in an autoclave at that temperature for crystallization. After full crystallinity was achieved, the resulting crystals were separated from remaining liquid by filtration, washed with water and dried. Analysis of the crystals confirmed the presence of zeolite ZSM-35.

A portion of the crystals was combined with alumina to form a mixture of 65 weight parts zeolite ZSM-35 and 35 weight parts alumina. Enough water was added to the mixture so that the resulting catalyst could be formed into an extrudate. The catalyst was activated by calcining first in nitrogen at 1000° F., followed by aqueous exchanges with 1.0 N ammonium nitrate solution and calcining in air at 1000 and 1200° F.

EXAMPLE 2

This example compares the catalytic performance of the alumina-bound ZSM-35 catalyst composition of Example 1 with ferrierite (Toyo Soda), also bound with 35 weight percent alumina, for the hydration of light olefin, specifically, propylene. The approximate crystal size of the two zeolites, as estimated, was less than about 0.2 microns in the case of ZSM-35 catalyst and from about 0.2 to about 1.0 microns in the case of the ferrierite catalyst.

The alumina-bound ZSM-35 and ferrierite compositions were each employed at two different mole ratios of water:propylene, namely 2:1 and 0.5:1, respectively. The other reaction conditions employed were 1000 psig, 330° F. and 0.6 WHSV based on propylene and zeolite. The results are set forth in Table 4 as follows:

TABLE 4

Comparison of ZSM-35 and Ferrierite in Propylene Hydration

|  | ZSM-35 | | Ferrierite | |
| --- | --- | --- | --- | --- |
| Mole Ratio Water: Propylene | 2:1 | 0.5:1 | 2:1 | 0.5:1 |
| Water Conversion, % | 25.3 | 46.2 | 0.5 | 3.9 |
| Propylene Conversion, % | 55.1 | 31.0 | 8.7 | 6.2 |
| Alcohol Selectivity, % | 99.5 | 99.3 | 98.7 | 99.6 |

EXAMPLES 3–13

Further comparisons were made between the catalytic performance of alumina-bound ZSM-35 (Examples 3–10) and alumina-bound ferrierite (Examples 11–13).

The conditions of each reaction and the results are set out in Table 5.

TABLE 5

Comparison of ZSM-35 and Ferrierite in the Hydration of Propylene

| REACTION CONDITIONS | EXAMPLE | | | | | | | | | | |
| --- | --- | --- | --- | --- | --- | --- | --- | --- | --- | --- | --- |
|  | 3 | 4 | 5 | 6 | 7 | 8 | 9 | 10 | 11 | 12 | 13 |
| Reactor Pressure (psig) | 1000.00 | 1000.00 | 1000.00 | 1000.00 | 1000.00 | 1000.00 | 1000.00 | 1000.00 | 1000.00 | 1000.00 | 1000.00 |
| Average Temperature (°F.) | 330.00 | 330.00 | 330.00 | 302.00 | 301.00 | 330.00 | 330.00 | 379.00 | 330.00 | 330.00 | 381.00 |
| Water: Propylene Molar Ratio | 2.00 | 0.50 | 0.50 | 0.50 | 2.10 | 2.00 | 2.70 | 2.00 | 2.00 | 0.50 | 2.00 |
| Time On Stream (hr) | 19.50 | 43.50 | 67.50 | 91.50 | 163.25 | 186.25 | 210.25 | 231.25 | 21.25 | 45.25 | 66.00 |
| Space Velocity (WHSV) | 0.62 | 0.62 | 0.63 | 0.62 | 0.30 | 0.62 | 0.23 | 0.63 | 0.63 | 0.63 | 0.63 |
| Space Velocity (LHSV) | 0.64 | 0.49 | 0.49 | 0.49 | 0.31 | 0.65 | 0.26 | 0.65 | 0.67 | 0.51 | 0.67 |
| Feed Composition, Wt. % | | | | | | | | | | | |
| Water | 48.84 | 20.03 | 19.39 | 19.63 | 47.61 | 48.78 | 53.81 | 48.60 | 47.48 | 20.90 | 47.82 |
| Propylene | 51.16 | 79.97 | 80.61 | 80.37 | 52.39 | 51.22 | 46.19 | 51.40 | 52.52 | 79.10 | 52.18 |
| Product Dist., Wt. % | | | | | | | | | | | |
| Water | 36.49 | 10.77 | 11.38 | 15.80 | 43.63 | 44.67 | 47.55 | 42.12 | 47.26 | 20.09 | 43.83 |
| Propylene | 23.00 | 55.18 | 58.17 | 69.22 | 42.15 | 38.37 | 27.37 | 37.25 | 47.97 | 74.20 | 43.58 |
| 2-Propanol | 40.31 | 33.82 | 30.25 | 14.98 | 14.23 | 16.84 | 25.00 | 20.27 | 4.71 | 5.70 | 12.46 |
| Hexenes | 0.07 | 0.10 | 0.06 | 0.00 | 0.00 | 0.03 | 0.04 | 0.25 | 0.00 | 0.00 | 0.02 |
| Isopropyl Ether | 0.13 | 0.13 | 0.15 | 0.00 | 0.00 | 0.08 | 0.03 | 0.11 | 0.06 | 0.02 | 0.11 |
| Reactant Conversions, % | | | | | | | | | | | |
| Total Conversion | 40.51 | 34.05 | 30.46 | 14.98 | 14.23 | 16.96 | 25.08 | 20.63 | 4.77 | 5.72 | 12.59 |
| Water | 25.27 | 46.23 | 41.32 | 19.49 | 8.36 | 8.41 | 11.63 | 13.35 | 0.47 | 3.90 | 8.35 |
| Propylene | 55.0 | 31.00 | 27.84 | 13.87 | 19.56 | 25.09 | 40.75 | 27.53 | 8.66 | 6.20 | 16.48 |
| Conversion To Ranges, % | | | | | | | | | | | |
| To C3's | 40.31 | 33.82 | 30.25 | 14.98 | 14.23 | 16.84 | 25.00 | 20.27 | 4.71 | 5.70 | 12.46 |
| To C6+ | 0.20 | 0.23 | 0.21 | 0.00 | 0.00 | 0.12 | 0.08 | 0.36 | 0.06 | 0.03 | 0.13 |
| Mass Balance Closures, % | | | | | | | | | | | |
| Total Mass Balance | 94.71 | 95.13 | 93.53 | 97.53 | 96.53 | 95.12 | 96.96 | 94.39 | 95.95 | 97.07 | 97.49 |
| Carbon Balance | 95.15 | 94.05 | 92.27 | 96.73 | 96.00 | 93.34 | 94.34 | 95.10 | 93.76 | 95.97 | 97.93 |
| Hydrogen Balance | 94.77 | 94.93 | 93.29 | 97.38 | 96.46 | 94.89 | 96.65 | 94.48 | 95.66 | 96.87 | 97.55 |
| Oxygen Balance | 94.25 | 99.41 | 98.75 | 100.84 | 97.10 | 96.98 | 99.20 | 93.63 | 98.37 | 101.24 | 97.01 |
| Product Selectivities | | | | | | | | | | | |
| 2-Propanol | 99.51 | 99.32 | 99.31 | 100.00 | 100.00 | 99.31 | 99.69 | 98.25 | 98.65 | 99.63 | 98.98 |
| Hexenes | 0.18 | 0.29 | 0.18 | 0.00 | 0.00 | 0.20 | 0.18 | 1.22 | 1.35 | 0.37 | 0.86 |
| Isopropyl Ether | 0.31 | 0.39 | 0.51 | 0.00 | 0.00 | 0.49 | 0.13 | 0.53 | — | — | — |

We claim:

1. A process for converting propylene to isopropyl alcohol which comprises contacting water with a feed comprising propylene at water:propylene mole ratio of at least about 0.5:1 under propylene hydration conditions in the presence of a hydration catalyst comprising an acidic zeolite having pore openings defined by: (1) a ratio of sorption of n-hexane to o-xylene, on a volume percent basis, of greater than about 3, which sorption is determined at a $P/P_o$ of 0.1 and at a temperature of 50° C. for n-hexane and 80° C. for o-xylene and (2) by the ability of selectively cracking 3-methylpentane (3MP) in preference to the doubly branched 2,3-dimethylbutane (DMB) at 1000° F. and 1 atmosphere pressure from a 1/1/1 weight ratio mixture of n-hexane/3-methyl-pentane/2,3-dimethylbutane, with the ratio of rate constants $k_{3MP}/k_{DMB}$ determined at a temperature of 1000° F. being in excess of about 2, the zeolite having a crystal size of not more than 0.2 micron, to produce isopropyl alcohol.

2. The process of claim 1 wherein the water:propylene ratio is from about 1:1 to about 10:1.

3. The process of claim 1 wherein the temperature is from about 200° to about 400° F.

4. The process of claim 3 wherein the temperature is from about 300° to about 400° F.

5. The process of claim 1 wherein the temperature is from about 300° to about 350° F.

6. The process of claim 1 wherein the total system pressure is at least about 5 atm.

7. The process of claim 1 wherein the total system pressure is at least about 20 atm.

8. The process of claim 1 wherein the total system pressure is at least about 40 atmospheres.

9. The process of claim 1 wherein the zeolite is ZSM-35.

10. The process of claim 1 wherein the zeolite is ferrierite.

11. The process of claim 1 wherein the zeolite is ZSM-22.

12. The process of claim 1 wherein the zeolite is ZSM-23.

13. The process of claim 1 wherein the zeolite is bound with silica as a binder.

14. The process of claim 1 in which the crystal size of the zeolite is less than $0.1\mu$.

15. The process of claim 1 in which at least part of the framework aluminum of the zeolite is substituted by a metal other than aluminum.

* * * * *